(12) United States Patent
Nakamura

(10) Patent No.: US 11,246,970 B2
(45) Date of Patent: Feb. 15, 2022

(54) BLOOD PROCESSING FILTER

(71) Applicant: ASAHI KASEI MEDICAL CO., LTD., Tokyo (JP)

(72) Inventor: Kazuhiko Nakamura, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 26 days.

(21) Appl. No.: 16/076,213

(22) PCT Filed: Feb. 6, 2017

(86) PCT No.: PCT/JP2017/004223
§ 371 (c)(1),
(2) Date: Aug. 7, 2018

(87) PCT Pub. No.: WO2017/141752
PCT Pub. Date: Aug. 24, 2017

(65) Prior Publication Data
US 2019/0175816 A1    Jun. 13, 2019

(30) Foreign Application Priority Data

Feb. 15, 2016 (JP) .............................. JP2016-025738

(51) Int. Cl.
*A61M 1/36* (2006.01)
*A61M 1/02* (2006.01)
(Continued)

(52) U.S. Cl.
CPC ............ *A61M 1/3635* (2014.02); *A61M 1/02* (2013.01); *A61M 1/0281* (2013.01); *B01D 39/1623* (2013.01); *B01D 67/0088* (2013.01); *B01D 69/02* (2013.01); *A61M 2202/0427* (2013.01); *A61M 2202/0439* (2013.01); *B01D 67/0002* (2013.01); *B01D 69/10* (2013.01);
(Continued)

(58) Field of Classification Search
None
See application file for complete search history.

(56) References Cited

U.S. PATENT DOCUMENTS 4,936,998 A       6/1990   Nishimura et al.
2004/0253204 A1  12/2004  Yagi et al.
(Continued)

FOREIGN PATENT DOCUMENTS

CN    103041714 A    4/2013
CN    103484357 A    1/2014
(Continued)

OTHER PUBLICATIONS

International Search Report for International Patent Application No. PCT/JP2017/004223 dated Mar. 7, 2017.
(Continued)

*Primary Examiner* — Clare M Perrin
(74) *Attorney, Agent, or Firm* — Greenblum & Bernstein, P.L.C.

(57) ABSTRACT

Provided is a blood processing filter comprising a container having two spouts serving as an inlet for a liquid to be processed and an outlet for the processed liquid, and a filtration medium contained in the container, the filtration medium comprising a filter material having different CWST values for one surface A and the other surface B.

16 Claims, 1 Drawing Sheet

(51) Int. Cl.
  *B01D 39/16* (2006.01)
  *B01D 67/00* (2006.01)
  *B01D 69/02* (2006.01)
  *B01D 69/10* (2006.01)

(52) U.S. Cl.
  CPC ...... *B01D 2323/02* (2013.01); *B01D 2325/14* (2013.01); *B01D 2325/16* (2013.01); *B01D 2325/18* (2013.01); *B01D 2325/36* (2013.01)

(56) References Cited

U.S. PATENT DOCUMENTS

| | | | |
|---|---|---|---|
| 2005/0247627 A1* | 11/2005 | Bormann | A61M 1/3633 210/641 |
| 2006/0169635 A1 | 8/2006 | Zambianchi et al. | |
| 2006/0180542 A1* | 8/2006 | Mari | A61M 1/3633 210/489 |
| 2008/0073294 A1 | 7/2008 | Zambianchi et al. | |
| 2012/0048799 A1 | 3/2012 | Na et al. | |
| 2012/0067821 A1* | 3/2012 | Chang | A61M 1/3635 210/651 |
| 2013/0327722 A1 | 12/2013 | Siddiqui et al. | |
| 2014/0299556 A1* | 10/2014 | Zambianchi | B01D 39/1623 210/767 |
| 2015/0328565 A1* | 11/2015 | Swaminathan | B01D 17/045 210/489 |
| 2016/0263297 A1* | 9/2016 | Suzuki | A61M 1/3496 |
| 2017/0112982 A1 | 4/2017 | Matsuura | |
| 2017/0216504 A1 | 8/2017 | Miyamoto et al. | |

FOREIGN PATENT DOCUMENTS

| | | |
|---|---|---|
| CN | 105032202 A | 11/2015 |
| EP | 2050457 A | 4/2009 |
| EP | 2818189 A | 12/2014 |
| EP | 3058965 A | 8/2016 |
| EP | 3202432 A | 8/2017 |
| JP | H04-212373 A | 8/1992 |
| JP | H06-051060 B | 7/1994 |
| JP | 2005-535425 A | 11/2005 |
| JP | 2007-527257 | 9/2007 |
| JP | 2008-522809 A | 7/2008 |
| JP | 2012-183237 A | 9/2012 |
| WO | 2003-011924 A | 2/2003 |
| WO | WO-2015056603 A1 * | 4/2015 ......... A61M 1/3496 |
| WO | 2016-006574 A | 1/2016 |
| WO | 2016-052618 A | 4/2016 |

OTHER PUBLICATIONS

International Preliminary Report on Patentability for International Patent Application No. PCT/JP2017/004223 dated Aug. 21, 2018.
European Search Report dated Jun. 27, 2019 in corresponding European Patent Application No. EP17753010.2.

* cited by examiner

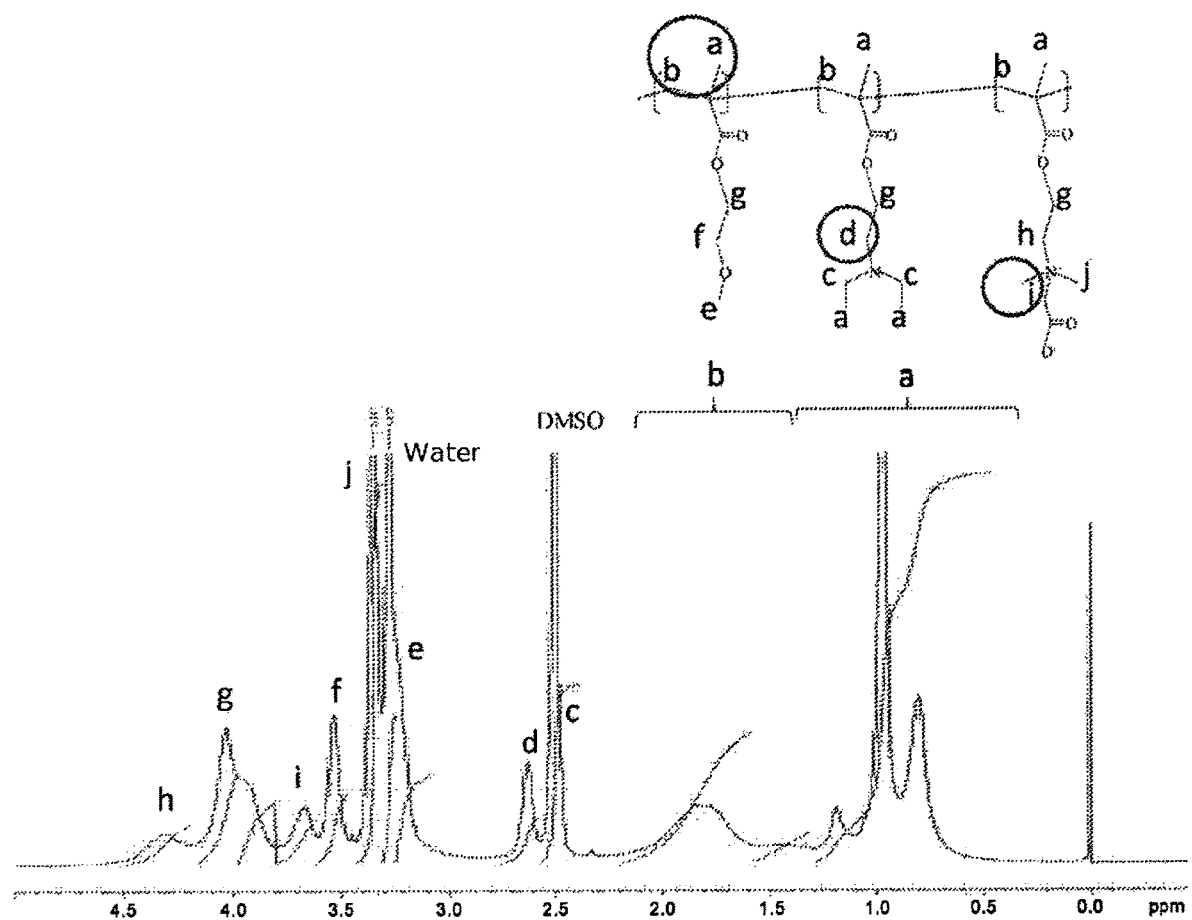

BLOOD PROCESSING FILTER

TECHNICAL FIELD

The present invention relates to a blood processing filter for removing undesirable components such as aggregates and white blood cells from blood and fluids containing blood components. More specifically, the present invention relates to a blood processing filter suitable for use as a disposable blood processing filter to remove side-effect causing microaggregates and white blood cells from, for example, whole blood products for blood transfusions, red blood cell products, platelet products, and plasma products.

BACKGROUND ART

In general, whole blood extracted from donors is used in transfusions after being separated into blood component products such as red blood cell products, platelet products, and plasma products, and then stored. Because microaggregates and white blood cells in these blood products are the cause of various blood transfusion side-effects, these undesirable components are either removed before transfusion or removed after extraction from donors and before temporary storage and transfusion.

Currently, two general methods are used to remove undesirable components such as white blood cells from blood products, namely, centrifugation in which differences in the specific gravities of blood cell components are utilized in a centrifuge to separate and remove undesirable components such as white blood cells, and filtration using a filtration medium (filter material) made of fiber aggregates such as nonwoven fabric or a porous structure with open cells. The filtration method is currently more popular because of advantages such as simple operation and low costs.

White blood cells are believed to be removed in the filtration method primarily by a mechanism in which white blood cells making contact with the filtration medium surface stick to or are adsorbed by the filtration medium surface. Therefore, in order to further improve white blood cell removal performance relative to that of conventional blood filtration filters, currently known methods include improving contact frequency between white blood cells and the filtration medium and increasing the per unit surface area of the filtration medium by reducing the fiber diameter and pore size to increase the bulk density. While these methods increase white blood cell removal performance, they are accompanied by greater pressure loss due to the filtration medium, resulting in lower flow rates and longer filtration times during blood processing.

Means that have been studied for reducing pressure loss include increasing affinity for white blood cells and improving wettability by modifying and treating the surfaces of filtration media with polymers. While these means hold down extended filtration times due to reduced pressure loss, they have difficulty maintaining good white blood cell removal performance.

CITATION LIST

Patent Literature

Patent Literature 1: JP 2003-517111 A
Patent Literature 2: JP 2011-049395 A

SUMMARY OF INVENTION

Technical Problem

It is an object of the present invention to provide a blood processing filter able to achieve high white blood cell removal performance with reduced filtration times.

Solution to Problem

The present inventors conducted extensive research in order to solve this problem and discovered that a blood processing filter combining high white blood cell removal performance with high blood flow performance could be obtained by using a filter material having different critical wetting surface tension (CWST) values for the front and rear surfaces as at least a portion of the filtration medium. The present invention is based on such a finding.

Specifically, the present invention is related to the following.

[1] A blood processing filter comprising a container having two spouts serving as an inlet for a liquid to be processed and an outlet for the processed liquid, and a filtration medium contained in the container, the filtration medium comprising a filter material having different critical wetting surface tension (CWST) values for one surface A and another surface B.

[2] A blood processing filter according to [1], wherein a CWST value for surface A of the filter material is 72 mN/m or more.

[3] A blood processing filter according to [1] or [2], wherein a difference in CWST values for surface A and surface B of the filter material is 3 mN/m or more.

[4] A blood processing filter according to any one of [1] to [3], wherein a ratio of a CWST value for surface A to a CWST value for surface B of the filter material is 1.03 or more.

[5] A blood processing filter according to any one of [1] to [4], wherein a CWST value for the one surface A is 72 mN/m or more and 110 mN/m or less, and a CWST value for the other surface B is 60 mN/m or more and 110 mN/m or less.

[6] A blood processing filter according to any one of [1] to [5], wherein the filtration medium comprises a filter material comprising a fibrous medium made of fibers having a fiber diameter of 4 μm or greater as a base material, and a filter material comprising a fibrous medium made of fibers having a fiber diameter of less than 4 μm as a base material.

[7] A blood processing filter according to any one of [1] to [6], wherein the filtration medium comprises a plurality of filter materials comprising a fibrous medium made of fibers having a fiber diameter of less than 4 μm as a base material, and wherein a CWST value for a surface of a filter material among the plurality of filter materials that is located closest to one spout of the container, such surface being on the side with the spout, is greater than a CWST value for a surface of a filter material among the plurality of filter materials that is located closest to the other spout of the container, such surface being on the side with the other spout.

[8] A blood processing filter according to any one of [1] to [7], wherein the filter material comprises nonwoven fabric.

[9] A blood processing filter according to any one of [1] to [8], wherein at least one of surface A and surface B has a polymer coating layer.

[10] A blood processing filter according to [9], wherein the polymer has a nonionic hydrophilic group and a basic nitrogen-containing functional group, and the amount of basic nitrogen atoms in the polymer coating layer is from 0.2 to 8.0 mass %.

[11] A blood processing filter according to [9], wherein the polymer has a functional group comprising a zwitterion.

[12] A blood processing filter according to [11], wherein the functional group comprising a zwitterion is a functional group derived from at least one type of compound selected from the group consisting of carbobetaine, sulfobetaine, and phosphobetaine.

[13] A blood processing filter according to [11] or [12], wherein the polymer comprises a monomer unit (l) having a nonionic group, a monomer unit (m) having a basic nitrogen-containing functional group, and a monomer unit (n) including a zwitterion.

[14] A method for manufacturing a blood processing filter according to any one of [9] to [13], the method comprising the steps of: preparing a filter base material; and coating at least one surface of the base material with the polymer using a gravure coating method.

[15] A filter material for a blood processing filter having different CWST values for one surface A and another surface B.

Advantageous Effects of Invention

A blood processing filter of the present invention has both good white blood cell removal performance and good blood flow performance, which are in a trade-off relationship, and are therefore able to simultaneously achieve high white blood cell removal and reduced filtration time.

BRIEF DESCRIPTION OF DRAWINGS

FIG. 1 shows an example of a $^1$H-NMR spectrum for a copolymer of an alkoxyalkyl (meth) acrylate, an N,N-dialkylaminoalkyl (meth) acrylate, and methyl methacrylate betaine.

DESCRIPTION OF EMBODIMENTS

The following is a detailed description of a mode for carrying out the present invention (referred to below as the "present embodiment"). Note that the present invention is not limited to the following description and many other variations can be embodied without departing from the spirit and scope of the present invention.

Critical surface tension is generally used as an indicator of the wettability of a solid surface. Critical surface tension indicates a surface tension of a liquid when the contact angle (θ) between the liquid and the solid is 0, and the solid surface does not cause expanding wetness even when it comes into contact with a liquid having a surface tension of at or above the critical surface tension. However, a porous material, such as a filtration medium, has a different critical surface tension from the critical surface tension value for the same material as measured on a flat solid. This is because the wettability of a porous body is believed to depend not only on the surface tension of the material itself but also on the pore size. Therefore, critical wetting surface tension (CWST) is used as an indicator of the wettability of a porous material (see JP H01-249063 A).

In the present embodiment, the CWST values of one surface A and another surface B of a filter material in the filtration medium are different.

The following method is used to measure the CWST value. A plurality of solutions whose surface tensions are known and different from each other are prepared by purchase or preparation. The surface tension of the prepared solution is measured using an automatic surface tensiometer (from Kyowa Interface Science, Wilhelmy plate method) in a standard testing room atmosphere (JIS K 7100) with a temperature of 23° C. and a relative humidity of 50%. Ten drops (10 μL per drop) of a solution having a certain surface temperature are placed gently on a flat surface and allowed to stand for 10 minutes. When the contact angle between the filtration medium and the solution is 90 degrees or less, it is determined that wetting was caused by the dropped solution. When nine or more of the ten drops cause wetting, the filtration medium is determined to be wet with the solution with the certain surface tension. When two or more of the ten drops do not cause wetting, the filtration medium is determined not to be wet with the solution of the certain surface tension.

When the filtration material is not wet with the solution, a solution having a surface tension that is 2 mN/m lower than the previously used solution is used. When the filtration material is wet with the solution, a solution having a surface tension that is 2 mN/m higher than the previously used solution is used. This operation is repeated to determine the maximum value among the surface tension of solutions that cause wetting and the minimum value among the surface tension of solutions that do not cause wetting. The average value of these is determined to be the CWST value for the substance.

When the measurements are conducted at a temperature and humidity other than 23° C. and 50% RH, a conversion table can be used, if such a conversion table exists, to convert the result to a CWST value at 23° C. and 50% RH.

In the present embodiment, for at least one filter material in the filtration medium, the CWST values (at 23° C. and 50% RH) of the front and rear surfaces of the filter material are different. Here, "the CWST values of the front and rear surfaces of the filter material are different" means the difference in the CWST values of the front and rear surfaces of the filter material are different by 1 mN/m or more.

In the present embodiment, surface A, which has the larger CWST value in the filter material, preferably has a value of 72 mN/m or more and 110 mN/m or less (72 dyn/cm or more and 110 dyn/cm or less). When the CWST value for a surface of a filtration medium is too low, it takes time to prime the filtration medium with blood, blood does not flow in the portions that are not primed with blood, and the filtration medium cannot be utilized effectively. When blood is processed at a high flow rate using a pump, unlike a case using a natural head difference, the blood is forcibly filtered in a narrow filtration area. In such a case, the load on red blood cells is great, which causes red blood cells to be destroyed, or hemolysis to occur. Therefore, when blood is filtered using a pump, the wettability of the filtration medium is preferably above a certain level. The CWST value for surface A, which has the larger CWST value, of the filter material in the filtration medium is preferably 72 mN/m or more so that the filtration medium can be quickly primed.

When the CWST value of one surface A of the filter material is 72 mN/m or more, more preferably 80 mN/m or more, and even more preferably 90 mN/m or more, the load on the red blood cells is reduced because the filtration medium is quickly filled with blood, hemolysis does not occur, and blood can be filtered in a short time. A higher CWST value for surface A is preferred to quickly fill the filtration medium with blood. However, from the standpoint of technical ease, a CWST value of 110 mN/m or less is preferred.

In the present embodiment, the CWST value for surface B, that is opposite to surface A in a filter material, is lower than the CWST value for surface A. The present inventors discovered that, by setting so, surface B, which tends to be hydrophobic, effectively traps undesirable components such as white blood cells while surface A, which tends to be hydrophilic, suppresses increased pressure loss, which can prevent extension of filtration times.

The difference in CWST values of the front and rear surface of the filter material is 3 mN/m or more, preferably 5 mN/m or more, and more preferably 10 mN/m or more. Also, the ratio of the CWST value of surface A to the CWST value of surface B is 1.03 or more, more preferably 1.05 or more, and even more preferably 1.10 or more. In addition, the CWST value for surface A is 72 mN/m or more and 100 mN/m or less, and the CWST value for surface B is 60 mN/m or more and 95 mN/m or less. When the CWST values of a filter material are within these ranges, the filter material quickly fills with blood and undesirable components such as white blood cells can be effectively trapped.

There are no particular restrictions on the method used to manufacture a filter material with different CWST values for the front and rear surfaces. One surface may be rendered hydrophilic using chemical treatment or plasma treatment, or at least one surface of the filter base material may be rendered hydrophilic or hydrophobic by coating the surface with a polymer to provide a polymer coating layer.

There are no particular restrictions on the method used to coat at least one surface of a filter base material with a polymer. In the present embodiment, an especially preferred method will be explained in which a surface of a filter base material is coated with a hydrophobic polymer using the gravure coating method.

The gravure coating method can be any conventional method used as a printing or coating technique. The present inventors discovered that a difference could be created between the CWST values for the front and rear surfaces of a filter material when a filter base material is coated with a hydrophilic polymer using a gravure roll by adjusting the distance between the gravure roll and a nip roll. In order to create a difference between the CWST values for the front and rear surfaces, the distance between the rolls is generally preferably from 50 to 400 µm, more preferably from 100 to 400 µm, and even more preferably from 200 to 400 µm, though it depends on the thickness of the filter base material. The distance between the gravure roll and the nip roll changes the pressure applied to the filter base material as it passes between the rolls. When the distance between the gravure roll and the nip roll is smaller, significant pressure is applied to the base material to wet its nip roll side with a polymer-containing solution, and the difference between the CWST values for the front and rear surfaces narrow. When the distance between the gravure roll and the nip roll is greater, the polymer-containing solution is less likely to reach the nip roll side, and thus a difference is created between the CWST values for the front and rear surfaces. However, when the distance between the gravure roll and the nip roll is too great, sufficient hydrophilicity cannot be imparted.

There are no particular restrictions on the hydrophilic polymer. However, use of a polymer having a nonionic hydrophilic group and a basic nitrogen-containing functional group is preferred. This is preferred because using such a polymer to render a surface of a filter material hydrophilic not only improves the wettability of the filter material but also improves blood cell trapping performance by introducing a charged functional group.

In the present embodiment, examples of nonionic hydrophilic groups include a hydroxyl group and an amide group.

Examples of monomers containing a nonionic hydrophilic group include monomers containing the hydroxyl group and amide group mentioned above such as 2-hydroxyethyl (meth) acrylate, 2-hydroxypropyl (meth) acrylate, vinyl alcohol (polymerized as vinyl acetate and then hydrolyzed), (meth) acrylamide, and N-vinyl pyrrolidone. Examples of a nonionic hydrophilic group include a polyethylene oxide chain in addition to the hydroxyl group and amide group mentioned above. Examples of monomers containing a polyethylene oxide chain include alkoxy polyethylene glycol (meth) acrylates such as methoxyethylene glycol (meth) acrylate, methoxydiethylene glycol (meth) acrylate, methoxytriethylene glycol (meth) acrylate, and methoxytetraethylene glycol (meth) acrylate. Among these monomers, use of 2-hydroxyethyl (meth) acrylate is preferred from the standpoint of availability, ease of handling during polymerization, and performance during the flow of blood.

Examples of basic nitrogen-containing functional groups include nitrogen-containing aromatics such as primary amino groups, secondary amino groups, tertiary amino groups and quaternary ammonium groups, as well as pyridine groups and imidazole groups. Examples of monomers containing basic nitrogen-containing functional groups include allylamines; derivatives of (meth) acrylic acid such as dimethylaminoethyl (meth) acrylate, dimethylaminopropyl (meth) acrylate, and 3-dimethylamino-2-hydroxyl (meth) acrylate; styrene derivatives such as p-dimethylaminomethylstyrene and p-dimethyl aminoethylstyrene; vinyl derivatives of nitrogen-containing aromatic compounds such as 2-vinylpyridine, 4-vinylpyridine, and 4-vinylimidazole; and quaternary ammonium salt derivatives that is obtained by subjecting the above described vinyl compounds to, for example, an alkyl halide. Among these monomers, dimethylaminoethyl (meth) acrylate and diethylaminoethyl (meth) acrylate are preferred from the standpoint of availability, ease of handling during polymerization, and performance during the flow of blood.

In the present embodiment, the basic nitrogen atom content of a polymer coating layer formed by these polymers is preferably from 0.2 to 8.0 mass %. By setting in this manner, the wettability of nonwoven fabric with blood can be improved.

When the basic nitrogen atom content is 0.2 mass % or more, the wettability of the filter with blood is higher and initial infiltration with blood is good. As a result, filtration time can be reduced. This can suppress a state known as one-sided flow in which the blood passes through the filtration medium only a portion where it can easily pass and the entire filtration medium is not used. As a result, filtration time is reduced and white blood cell removal performance is improved. In contrast, when the basic nitrogen atom content is 8.0 mass % or less, hemolysis of red blood cells due to the clogging of the passage between fibers with coating agent is more likely to be prevented.

The basic nitrogen atom content in the case of whole blood products is preferably from 0.2 to 8.0 mass % and more preferably from 0.3 to 7.0 mass %. In the case of platelet products, the content is preferably from 0.2 to 4.0 mass % in order to improve selective separability of platelets from white blood cells.

The basic nitrogen atom content can be calculated by immersing the filter material in a solvent such as EtOH to extract the polymer coating, and measuring the nitrogen content of the material dried by evaporation using, for example, elemental analysis. The presence of nonionic hydrophilic groups and basic nitrogen-containing functional groups can be determined by analyzing the surface of the filter material using Attenuated total reflection infrared spectroscopy (ATR-IR) or time-of-flight secondary ion mass spectrometry (TOF-SIMS).

In the present embodiment, a filter material having different CWST values for the front and rear surfaces can be obtained by coating at least one surface of the filter base material with a polymer containing a functional group including zwitterion. Examples of the functional group including zwitterion are represented in general formulas (1) to (3) below.

[Formula 1]

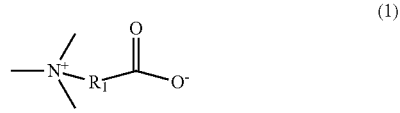

(1)

In general formula (1), $R_1$ is an alkyl group with at least one carbon atom.

[Formula 2]

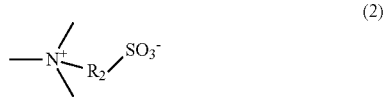

(2)

In general formula (2), $R_2$ is an alkyl group with at least one carbon atom.

[Formula 3]

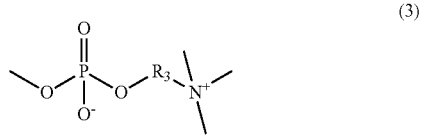

(3)

In general formula (3), $R_3$ is an alkyl group with at least one carbon atom.

The functional groups including zwitterion represented by general formulas (1), (2), and (3) are derived, respectively, from carbobetaines (betaines having a carboxyl group), sulfobetaines (betaines having a sulfonic acid group), and phosphobetaines (betaines having a phosphonic acid group). From the standpoint of economy, a functional group derived from a methyl methacrylate betaine represented by general formula (4) is preferred.

[Formula 4]

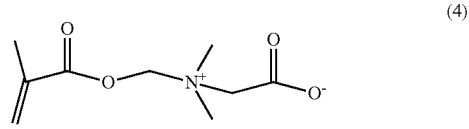

(4)

From the standpoint of realizing better hemolysis prevention, the ratio of monomer units having a functional group including zwitterion based on all monomer units in the coating polymer is preferably 1.5% or more. The ratio of monomer units having a functional group including zwitterion based on all monomer units is obtained by extracting the polymer in a soluble solvent and calculating the ratio using a combination of a nuclear magnetic resonance (NMR) measurement and amino group amount measurement.

Functional groups including zwitterion are preferably in side chains.

The coating polymer is preferably a copolymer with a monomer having a functional group including zwitterion and a monomer having a basic nitrogen-containing functional group. The copolymer may be a random copolymer or a block copolymer.

Examples of nonionic groups include alkyl groups, alkoxy groups, a carbonyl group, an aldehyde group, and a phenyl group.

Typical examples of compounds having a nonionic group include alkoxyalkyl (meth) acrylates, but 2-methoxyethyl (meth) acrylate is preferred from the standpoint of availability and economy.

Examples of the basic nitrogen-containing functional groups are described above, and preferred examples include amino groups represented by —$NH_2$, —$NHR_1$, —$NR_2R_3$, and —$N^+R_4R_5R_6$ (where $R_1$, $R_2$, $R_3$, $R_4$, $R_5$, and $R_6$ are alkyl groups having from 1 to 3 carbon atoms).

Typical examples of compounds having a basic nitrogen-containing functional group include N,N-dialkylaminoalkyl (meth) acrylates, and among them, N,N-diethylaminoethyl (meth) acrylate is preferred from the standpoint of availability and economy.

In filters used to remove white blood cells and/or platelets, the coating polymer preferably consists of a monomer unit having a nonionic group, a monomer unit having a basic nitrogen-containing functional group, and a monomer unit having a functional group including zwitterion, and does not contain other monomer unit. In other words, when the molar ratio of all monomers constituting the coating polymer is 100, the molar ratio of monomer units having a nonionic group (i), monomers units having a basic nitrogen-containing functional group (m), and monomer units having a functional group including zwitterions (n) in the coating polymer is l+m+n=100, where 0<l, m, n<100. When the molar ratio is within this range, excellent white blood cell removal performance and platelet removal performance can be realized while also suppressing damage such as hemolysis of red blood cells.

When the molar ratio of monomer units having a functional group including zwitterion is greater than 32.5% and the molar ratio of monomer units having a basic nitrogen-containing functional groups is less than 1.5%, there is no problem with hemolysis of red blood cells but white blood cell removal performance and platelet removal performance tend to decline. From the standpoint of achieving better white blood cell removal performance and platelet removal performance while maintaining a hemolysis preventing effect, the molar ratio of monomer units having a nonionic group, monomers units having a basic nitrogen-containing functional group, and monomer units having a functional group including zwitterion in the coating polymer is preferably 40-97/1.5-32.5/1.5-32.5, more preferably 40-95/2.5-30/2.5-30, even more preferably 50-95/2.5-30/2.5-30, and still more preferably 60-95/2.5-30/2.5-30.

The procedure to measure and calculate the molar ratio of monomer units having a nonionic group, monomers units having a basic nitrogen-containing functional group, and monomer units having a functional group including zwitterion in the coating polymer is explained below using an example consisting of alkoxyalkyl (meth) acrylate, N,N-dialkylaminoalkyl (meth) acrylate, and methyl methacrylate betaine. First, the coating polymer is dissolved in an appropriate solvent such as dimethylsulfoxide and measured using proton nuclear magnetic resonance ($^1$H-NMR). Using the resulting $^1$H-NMR, the total amount of monomer units is determined from the peaks attributable to H included in all of the monomer units (peaks a and b in the example shown in FIG. 1, which will be described below). Next, from the peak (d) attributable to H in the N,N-dialkylaminoalkyl (meth) acrylate monomer unit and the peak (i) attributable to H in the methyl methacrylate betaine monomer unit, the amount of each monomer unit is determined. The amount for the alkoxyalkyl (meth) acrylate monomer is obtained by subtracting the amounts of the two other monomer units from the total amount for all monomer units, and the molar ratio of alkoxyalkyl (meth) acrylate monomer unit, N,N-dialkylaminoalkyl (meth) acrylate monomer unit, and methyl methacrylate betaine monomer unit in the coating polymer is calculated.

In the present embodiment, a filtration medium includes at least one filter material having different CWST values for the front and rear surfaces, the filtration medium may be a single unit of such a filtration material, a laminate consisting of multiple layers of such filter materials, or a laminate consisting of one or more filter materials having different CWST values for the front and rear surfaces and one or more filter materials having the same CWST value for both the front and rear surfaces. In these cases, the filtration material can be considered as a minimum unit of the laminate structure constituting the filtration medium.

In the present embodiment, there are no particular restrictions on the shape of the filtration medium. For example, it can be a flat laminate of filter materials, or the cylindrical molded body thereof (for example, a spiral-shaped laminate). The former is commonly used in transfusion filters because the shape is compact and relatively simple. The latter is preferably used in filters for extracorporeal circulation because it is suitable for processing large amounts of liquid.

In the present embodiment, when a filter material has a polymer coating layer on at least one surface of the filter material, the polymer is preferably carried in an amount of 1.0 mg or more per 1 g of filter material (the total for both the filter material and the polymer coating layer).

In the present embodiment, the blood processing filter includes a filtration medium and a container filled with (accommodating) the filtration medium. There are no particular restrictions on the container accommodating the filtration medium in the blood processing filter as long as the container has two spouts, namely, an inlet for the liquid to be processed (blood or a liquid containing blood components) and an outlet for the processed liquid (a liquid (or blood) with undesirable components such as white blood cells removed). When the filtration medium is flat, the profile of the container can be polygonal such as rectangular or hexagonal, or curved such as round or oval-shaped depending on the shape of the filtration medium. When the filtration medium is cylindrical, the container can be a cylinder. There are no particular restrictions on the container material, which can be a hard material or a flexible material.

The filtration medium is usually arranged inside the container so that the interior of the container is separated into an inlet side and an outlet side.

There are no particular restrictions on the arrangement of the filtration material inside the container. Surface A (the surface with the higher CWST value) and surface B of the filter material in the filtration medium may be arranged to face either the inlet side or the outlet side. For example, it may be arranged inside the container so that surface A faces the inlet side and surface B faces the outlet side. When the hydrophilic surface A with the higher CWST value is arranged on the inlet side of the container, the filtration material is more likely to fill quickly with blood. When the hydrophobic surface B with the lower CWST value is arranged on the outlet side of the container, undesirable components such as white blood cells are effectively trapped. Therefore, this arrangement is preferred.

In the present embodiment, there are no particular restrictions on the structure of the filter base material constituting the filter material as long as the pore size enables blood to be filtered. Preferred structures include fibrous media such as natural fibers, glass fibers, knitted fabric, woven fabric, and nonwoven fabric, porous membranes, and spongy structures having a three-dimensional network of open cells.

There are no particular restrictions on the material of the filter base material as long as the material does not damage blood cells. Examples include organic polymer materials, inorganic polymer materials, and metals. Organic polymer materials are preferred because they can be processed more effectively, such as being cut. Examples include polyesters, polyolefins, polyacrylonitriles, polyamides, polystyrenes, polymethyl methacrylate, polyvinyl fluoride, polyurethanes, polyvinyl alcohols, polyvinyl acetals, polysulfones, polyvinylidene fluoride, polytrifluorochlorovinyl, vinylidene fluoride-tetrafluoroethylene copolymers, polyethersulfone, polyacrylates, butadiene-acrylonitrile copolymers, polyether-polyamide block copolymers, ethylene-vinyl alcohol copolymers, cellulose, and cellulose acetate. The material is not limited to these examples. Polyesters and polyolefins are preferred, and polyesters are especially preferred.

The filtration medium may be composed of a single filter material or a plurality of filter materials. In the case of being composed of a plurality of filter materials, the same type or different types of filter materials may be used.

When the filtration medium is made of a plurality of filter materials, different types of filter materials (for example, filter materials whose base materials are fibrous media with different fiber diameter ranges) are preferably used to perform different roles.

In a specific example, a pre-filter material can be used primarily to remove minute aggregates on the upstream side (that is, near the inlet to the container for the liquid to be processed), and a main filter material can be used to remove undesirable components other than microaggregates (primarily foreign matter) on the downstream side (that is, near the outlet from the container for the processed liquid). One or more pre-filter materials and main filter materials may be used. In this case, the pre-filter material can be a fibrous medium made of fibers having a fiber diameter of 4 μm or more, and the main filter material can be a fibrous medium made of fibers having a fiber diameter of less than 4 μm. Here, the fiber diameter of the fibrous base materials is determined using the following process. First, a portion of the fibrous base material is sampled and photographed using a scanning electron microscope. When sampling, the fibrous base material (or an effective cross-section of the filtration medium if already included in a filtration medium) is divided into square-shaped sections having a side length of 0.5 cm and six of the sections are randomly sampled. Each of these sections is observed at a magnification power of 2500×. Photographs are taken for each section at or near the center of the sample so that the total number of fibers photographed in each section is 100 or more. The diameters of all of the fibers visible in these photographs are measured. Here, the diameter refers to the width of a fiber in the direction perpendicular to the axis of the fiber. The average fiber diameter obtained by dividing the sum of the diameters of all measured fibers by the number of fibers is used as the fiber diameter. Here, when a plurality of fibers are overlapped so that the diameter of a fiber hidden behind another fiber cannot be measured, when a plurality of fibers are melted, for example, to form a thick fiber, when fibers significantly differing in diameter coexist, such data is not counted.

For example, one or more pre-filter materials having a fiber diameter of from 4 to 40 μm may be arranged near the inlet to remove aggregates, then one or more main filter materials including nonwoven fabric having a fiber diameter of from 0.3 to 3.0 μm may be laminated to remove undesirable components other than aggregates, and further a post-filter material having a specific pore diameter may then be laminated.

When multiple main filter materials, pre-filter materials, and post-filter materials are used, each one may be the same type or a different type of filter material. For example, two types of pre-filter material made of a nonwoven fabric having a fiber diameter of from 30 to 40 μm and a nonwoven fabric having a fiber diameter of from 10 to 20 μm may be arranged upstream, and two types of main filter material made of a nonwoven fabric having a fiber diameter of from 1.5 to 2.5 μm and a nonwoven fabric having a fiber diameter of from 0.5 to 1.8 μm may be arranged downstream from the pre-filter materials. When multiple pre-filter materials and main filter materials are used, the materials may be arranged in alternating fashion. However, in this case, pre-filter materials are preferably arranged first on the upstream side.

A filter material having different CWST values for the front and rear surfaces may be included anywhere in a filtration medium. For example, it may be included in the pre-filter material, the main filter material, or the post-filter material, or it may be included in all of them.

Moreover, when a plurality of filter materials are comprised as the main filters, a CWST value on a surface of a filter material among the plurality of main filter materials that is located closest to one spout of the container (for example, the inlet), such surface being on the side with the spout (on the inlet side), may be higher than a CWST value for a surface of a filter material among the plurality of main filter materials that is located closest to the other spout (for example, the outlet) of the container, such surface being on the side with the other spout (on the outlet side).

In addition, the filter materials may be arranged so that the CWST values of the surfaces of the filter materials decrease continuously or in stages while repeatedly moving up and down from one spout side to the other spout side (for example, from the inlet to the outlet).

In the situation above, the filtration medium can more quickly fill with blood when, for example, hydrophilic surface A with a higher CWST value is arranged on the inlet side of the container. Meanwhile, the filtration medium can more effectively trap undesirable components such as white blood cells when hydrophobic surface B with a lower CWST value is arranged on the outlet side of the container.

EXAMPLES

The following is a more detailed description of the present invention using examples. The present invention is not limited in any way by the following examples. The numerical values used in the examples and comparative examples were measured using the following methods.

(Measurement of CWST Values)

The CWST values of one surface A and the other surface B of a filtration medium were measured with the method described above using an acetic acid aqueous solution (from 54 to 70 mN/m) and a sodium hydroxide aqueous solution (from 72 to 100 mN/m).

(Creation of a Filtration Medium)

For the filter materials, 8 sheets of polyester nonwoven fabric P having an average fiber diameter of 12 μm, a mass per unit area of 30 g/m$^2$, and a specific surface area of 0.24 m$^2$/g, 2 sheets of polyester nonwoven fabric X having an average fiber diameter of 1.8 μm, a mass per unit area of 60 g/m$^2$, and a specific surface area of 1.1 m$^2$/g, and 32 sheets of polymer coated polyester nonwoven fabric Y, which is obtained by coating a polymer on a polyester nonwoven fabric prepared in each of the examples and comparative examples having an average fiber diameter of 1.2 μm, a mass per unit area of 40 g/m$^2$, and a specific surface area of 1.47 m$^2$/g, were prepared. Filter materials P, X and Y were laminated from the upstream side in the order P (4 sheets)/X (1 sheet)/Y (32 sheets) [or Y1 (16 sheets)/Y2 (16 sheets) when two types of Y are used]/X (1 sheet)/P (4 sheets) to create a filtration medium in the form of a laminate. Filter materials Y were laminated in the same direction when the front surface and the rear surface had different values. The filtration medium was interposed between two flexible vinyl chloride resin sheets having a port forming the blood inlet or outlet, and the peripheral edges of the filtration medium and the flexible sheets were fused and integrated using a high-frequency fusing device to produce a blood processing filter having an effective filtration area of 43 cm$^2$. Prior to the white blood cell removal performance test described below, the blood processing filter was subjected to high pressure steam sterilization for 59 minutes at 115° C.

(White Blood Cell Removal Performance Test)

Using a red blood cell product prepared in accordance with European standards as a blood product, filtration and removal were performed using the blood processing filters in Examples 1-5 and Comparative Examples 1-7 by means of a 100 cm natural head difference to obtain a filtered blood product.

(White Blood Cell Removal Performance)

White blood cell removal performance was calculated using the following equation.

White blood cell removal performance=−log [(white blood cell concentration in filtered blood product)/(white blood cell concentration in unfiltered blood product)]

Note that the white blood cell concentrations in the blood product before and after filtration were measured using a Becton Dickinson (BD) LeucoCOUNT white blood cell enumeration kit and a BD FACSCantoII flow cytometer.

Example 1

A polymerization solution (39 mass % copolymer concentration, ethanol solution) containing a copolymer composed of 97 mol % 2-hydroxyethyl (meth) acrylate and 3 mol % dimethylaminoethyl (meth) acrylate (weight average molecular weight: 570,000; basic nitrogen atom content: 0.32 mass %, nonionic hydrophilic groups: 97 mol %, amount of basic nitrogen atoms: 3 mol %, peak top molecular weight: 3.75×10$^5$, low molecular weight component content: 26.0%) was prepared. To the polymerization solution, ethanol in an amount four times the volume of the polymerization solution was added and uniformly dissolved at 40° C. This solution was allowed to stand for 12 hours at 25° C., and then liquid-liquid phase separation was performed using a thermally induced phase separation method to separate and recover only a polymer-rich phase solution (copolymer concentration: 31 mass %).

Ethanol was added to the polymer-rich phase solution and dissolved at 40° C. to prepare a uniform polymer coating solution with a copolymer concentration of 1.68 mass %.

Using the polymer coating solution prepared above, polyester nonwoven fabric having an average fiber diameter of 1.2 µm, a mass per unit area of 40 g/m², and a specific surface area of 1.47 m²/g was coated by being continuously passed between a gravure roll and a nip roll. The distance between the gravure roll and the nip roll was set at 300 µm. The coated nonwoven fabric was passed through a first drying chamber at 40° C. and a second drying chamber at 60° C., and then was rolled up into a roll and 32 sheets of filter material were cut out to be used as filter material Y. The line speed was fixed at 10 m/min.

The CWST values of the filter material were 91 mN/m for the one surface A and 77 mN/m for the other surface B.

The white blood cell removal performance test described above was performed on a blood processing filter using this filter material Y. The white blood cell removal performance was 3.7 Log and the filtration time was 25.0 minutes. Both the white blood cell removal performance and the filtration time were improved over Comparative Example 1.

Example 2

From nonwoven fabric that was coated and dried in the same manner as Example 1 except that the distance between the gravure roll and the nip roll was set to 400 µm, 16 sheets of filter material 1 were cut out. The CWST values of the filter material 1 were 95 mN/m for the one surface A and 81 mN/m for the other surface B.

In the same manner as Example 1, 16 sheets of filter material 2 were prepared.

The resulting filter materials 1 and 2 were used as filter materials Y1 and Y2. The white blood cell removal performance test described above was performed, and the white blood cell removal performance was 3.7 Log and the filtration time was 20.4 minutes. Both the white blood cell removal performance and the filtration time were improved over Comparative Example 2.

Example 3

From nonwoven fabric that was coated and dried in the same manner as Example 1 except that the distance between the gravure roll and the nip roll was set to 120 µm, 32 sheets of filter material were cut out. The CWST values of the resulting filter material were 91 mN/m for the one surface A and 81 mN/m for the other surface B. This was used as filter material Y.

The white blood cell removal performance test described above was performed, and the white blood cell removal performance was 3.6 Log and the filtration time was 24.8 minutes. Both the white blood cell removal performance and the filtration time were improved over Comparative Example 1.

Example 4

From nonwoven fabric that was coated and dried in the same manner as Example 1 except that the distance between the gravure roll and the nip roll was set to 200 µm, 16 sheets of filter material 1 were cut out. The CWST values of the filter material were 95 mN/m for the one surface A and 85 mN/m for the other surface B.

In the same manner as Example 2, sheets of filter material 2 were prepared.

The resulting filter materials 1 and 2 were used as filter materials Y1 and Y2. The white blood cell removal performance test described above was performed, and the white blood cell removal performance was 3.5 Log and the filtration time was 21.0 minutes. Both the white blood cell removal performance and the filtration time were improved over Comparative Example 2.

Example 5

From nonwoven fabric that was coated and dried in the same manner as Example 1 except that the distance between the gravure roll and the nip roll was set to 50 µm, 32 sheets of filter material were cut out. The CWST values of the resulting filter material were 90 mN/m for the one surface A and 87 mN/m for the other surface B. This was used as filter material Y.

The white blood cell removal performance test described above was performed, and the white blood cell removal performance was 3.4 Log and the filtration time was 24.9 minutes. Both the white blood cell removal performance and the filtration time were improved over Comparative Example 1.

Example 6

From nonwoven fabric that was coated and dried in the same manner as Example 1 except that the distance between the gravure roll and the nip roll was set to 100 µm, 16 sheets of filter material 1 were cut out. The CWST values of the filter material 1 were 95 mN/m for the one surface A and 92 mN/m for the other surface B.

In the same manner as Example 5, sheets of filter material 2 were prepared. The resulting filter materials 1 and 2 were used as filter materials Y1 and Y2.

The white blood cell removal performance test described above was performed, and the white blood cell removal performance was 3.3 Log and the filtration time was 20.6 minutes. Both the white blood cell removal performance and the filtration time were improved over Comparative Example 2.

Example 7

A copolymer of 2-methoxyethyl (meth) acrylate (MEMA), N,N-diethylaminoethyl (meth) acrylate (DEAEMA), and methyl methacrylate betaine (CMB) was synthesized using ordinary solution polymerization method. As for the polymerization conditions, the polymerization reaction was conducted for eight hours at 60° C. in an ethanol solution containing each monomer at a concentration of 1 mol/L in the presence of 0.0025 mol/L of an azoisobutyronitrile (AIBN) initiator. The resulting polymerization solution was instilled in water and the precipitated polymer was recovered. The recovered polymer was pulverized and dried for 24 hours under reduced pressure to obtain a polymer for coating.

The molar ratio of the 2-methoxyethyl (meth) acrylate monomer unit, N,N-diethylaminoethyl (meth) acrylate monomer unit, and methyl methacrylate betaine monomer unit in the polymer for coating were calculated by dissolving the polymer in dimethylsulfoxide and conducting an $^1$H-NMR measurement. The $^1$H-NMR chart of the polymer for coating with peaks attributed to each H atom are shown in FIG. 1. As a result of calculating the molar ratio of the H atoms in f, d and i, the molar ratio of the 2-methoxyethyl (meth) acrylate monomer unit, N,N-diethylaminoethyl (meth) acrylate monomer unit, and methyl methacrylate betaine monomer unit is 70/10/20.

After adding the polymer for coating to 90 W/W % ethyl alcohol, the solution was stirred for 12 hours to prepare a uniform polymer coating solution with a coating polymer concentration of 0.56 mass %.

The polymer coating solution prepared above was used to coat polyester nonwoven fabric having an average fiber diameter of 1.2 μm, a mass per unit area of 40 g/m$^2$, and a specific surface area of 1.47 m$^2$/g was coated by being continuously passed between a gravure roll and a nip roll. The distance between the gravure roll and the nip roll was set at 100 μm. The coated nonwoven fabric was passed through a first drying chamber at 40° C. and a second drying chamber at 60° C., and then was rolled up into a roll and 16 sheets of filter material 1 were cut out. The line speed was fixed at 10 m/min.

The CWST values of the filter material 1 were 80 mN/m for the one surface A and 76 mN/m for the other surface B.

From nonwoven fabric that was coated and dried in the same manner as Example 1 except that the distance between the gravure roll and the nip roll was set to 120 μm, and from the resulting nonwoven fabric, 16 sheets of filter material 2 were cut out. The CWST values of the filter material 2 were 78 mN/m for the one surface A and 73 mN/m for the other surface B.

The resulting filter materials 1 and 2 were used as filter materials Y1 and Y2. The white blood cell removal performance test described above was performed, and the white blood cell removal performance was 4.0 Log and the filtration time was 26.8 minutes. Both the white blood cell removal performance and the filtration time were improved over Comparative Example 3.

Comparative Example 1

Polyester nonwoven fabric having an average fiber diameter of 1.2 μm, a mass per unit area of 40 g/m$^2$, and a specific surface area of 1.47 m$^2$/g was continuously immersed in the polymer coating solution prepared in Example 1 and then passed between nip rolls. The coated nonwoven fabric was dried in the same manner as Example 1, 32 sheets of filter material were cut out, and used as filter material Y.

The CWST values of the filter material 1 were 88 mN/m for the one surface A and 88 mN/m for the other surface B.

The white blood cell removal performance test described above was performed, and the white blood cell removal performance was 3.1 Log and the filtration time was 25.8 minutes.

Comparative Example 2

From nonwoven fabric that was coated and dried in the same manner as Comparative Example 1 except that the concentration of the polymer coating solution was 1.5 times greater than the polymer coating solution used in the coating process in Example 1, 16 sheets of filter material 1 were cut out. The CWST values of the filter material 1 were 95 mN/m for the one surface A and 95 mN/m for the other surface B.

In the same manner as Comparative Example 1, sheets of filter material 2 were prepared.

The resulting filter materials 1 and 2 were used as filter materials Y1 and Y2. The white blood cell removal performance test described above was performed, and the white blood cell removal performance was 2.9 Log and the filtration time was 20.8 minutes.

Comparative Example 3

From nonwoven fabric that was coated and dried in the same manner as Comparative Example 1 except that the polymer coating solution prepared in Example 7, 16 sheets of filter material 1 were cut out. The CWST values of the filter material 1 were 78 mN/m for the one surface A and 78 mN/m for the other surface B.

From nonwoven fabric that was coated and dried in the same manner as Comparative Example 1 except that the concentration of the polymer coating solution was 0.75 times the polymer coating solution used in Example 7, 16 sheets of filter material 2 were cut out. The CWST values of the filter material 2 were 75 mN/m for the one surface A and 75 mN/m for the other surface B.

The resulting filter materials 1 and 2 were used as filter materials Y1 and Y2. The white blood cell removal performance test described was performed, and the white blood cell removal performance was 3.5 Log and the filtration time was 27.0 minutes.

[Overall Assessment]

As shown in Table 1 below, by using filter materials with different CWST values for the front and rear surfaces, undesirable components such as white blood cells can be effectively captured, increase in pressure loss can be suppressed, and increase in filtration time can be prevented. As a result, white blood cell removal performance and filtration time are improved relative to the comparative examples.

The results from the examples and comparative examples are shown in Table 1.

TABLE 1

| | | | | Examples | | | | | | | Comparative Examples | | |
|---|---|---|---|---|---|---|---|---|---|---|---|---|---|
| | | | | 1 | 2 | 3 | 4 | 5 | 6 | 7 | 1 | 2 | 3 |
| Filter Material Y | 1 | CWST Value | Surface A | 91 | 95 | 91 | 95 | 90 | 95 | 80 | 88 | 95 | 78 |
| | | [mN/m] | Surface B | 77 | 81 | 81 | 85 | 87 | 92 | 76 | 88 | 95 | 78 |
| | | CWST Value Difference | | 14 | 14 | 10 | 10 | 3 | 3 | 4 | 0 | 0 | 0 |
| | | CWST Value Ratio | | 1.18 | 1.17 | 1.12 | 1.12 | 1.03 | 1.03 | 1.05 | 1.00 | 1.00 | 1.00 |
| | 2 | CWST Value | Surface A | — | 91 | — | 91 | — | 90 | 78 | — | 88 | 75 |
| | | [mN/m] | Surface B | — | 77 | — | 81 | — | 87 | 73 | — | 88 | 75 |
| | | CWST Value Difference | | — | 14 | — | 10 | — | 3 | 5 | — | 0 | 0 |
| | | CWST Value Ratio | | — | 1.18 | — | 1.12 | — | 1.03 | 1.07 | — | 1.00 | 1.00 |
| Leukocyte Removal Performance [Log] | | | | 3.7 | 3.7 | 3.6 | 3.5 | 3.4 | 3.3 | 4.0 | 3.1 | 2.9 | 3.5 |
| Processing Time [min] | | | | 25.0 | 20.4 | 24.8 | 21.0 | 24.9 | 20.6 | 26.8 | 25.8 | 20.8 | 27.0 |

INDUSTRIAL APPLICABILITY

A blood processing filter of the present invention can be used to remove undesirable components such as aggregates and white blood cells from blood and fluids containing blood components. The present invention is especially suitable for use as a disposable blood processing filter to remove side-effect causing microaggregates and white blood cells from, for example, whole blood products for blood transfusions, red blood cell products, platelet products, and plasma products.

The present application is based on a Japanese patent application (Patent Application No. 2016-025738) filed with the Japan Patent Office on Feb. 15, 2016, the contents of which are incorporated herein by reference.

The invention claimed is:

1. A blood processing filter comprising:
    a container having two spouts serving as an inlet for a liquid to be processed and an outlet for the processed liquid; and
    a filtration medium contained in the container,
    the filtration medium comprising a plurality of layers of filter materials, each layer having one surface A and another surface B,
    both the surface A and surface B are hydrophilic polymer coating layers, and
    the surface A and the surface B having different critical wetting surface tension (CWST) values.

2. A blood processing filter according to claim 1, wherein a CWST value for surface A in each layer of the filter materials is 72 mN/m or more.

3. A blood processing filter according to claim 1, wherein a difference in CWST values for surface A and surface B in each layer of the filter materials is 3 mN/m or more.

4. A blood processing filter according to claim 3, wherein the filtration medium comprises a plurality of filter materials comprising a fibrous medium made of fibers having a fiber diameter of less than 4 μm as a base material,
    and wherein a CWST value for a surface of a layer of a filter material among the plurality of filter materials that is located closest to one spout of the container, such surface being on the side with the spout, is greater than a CWST value for a surface of a layer of a filter material among the plurality of filter materials that is located closest to the other spout of the container, such surface being on the side with the other spout.

5. A blood processing filter according to claim 1, wherein a ratio of a CWST value for surface A to a CWST value for surface B in each layer of the filter materials is 1.03 or more.

6. A blood processing filter according to claim 5, wherein the filtration medium comprises a plurality of filter materials comprising a fibrous medium made of fibers having a fiber diameter of less than 4 μm as a base material,
    and wherein a CWST value for a surface of a layer of a filter material among the plurality of filter materials that is located closest to one spout of the container, such surface being on the side with the spout, is greater than a CWST value for a surface of a layer of a filter material among the plurality of filter materials that is located closest to the other spout of the container, such surface being on the side with the other spout.

7. A blood processing filter according to claim 1, wherein a CWST value for the one surface A is 72 mN/m or more and 110 mN/m or less, and a CWST value for the other surface B is 60 mN/m or more and 110 mN/m or less.

8. A blood processing filter according to claim 7, wherein the filtration medium comprises a plurality of filter materials comprising a fibrous medium made of fibers having a fiber diameter of less than 4 μm as a base material,
    and wherein a CWST value for a surface of a layer of a filter material among the plurality of filter materials that is located closest to one spout of the container, such surface being on the side with the spout, is greater than a CWST value for a surface of a layer of a filter material among the plurality of filter materials that is located closest to the other spout of the container, such surface being on the side with the other spout.

9. A blood processing filter according to claim 1, wherein the filtration medium comprises a filter material comprising a fibrous medium made of fibers having a fiber diameter of 4 μm or greater as a base material, and a filter material comprising a fibrous medium made of fibers having a fiber diameter of less than 4 μm as a base material.

10. A blood processing filter according to claim 1, wherein the filtration medium comprises a plurality of filter materials comprising a fibrous medium made of fibers having a fiber diameter of less than 4 μm as a base material,
    and wherein a CWST value for a surface of a layer of a filter material among the plurality of filter materials that is located closest to one spout of the container, such surface being on the side with the spout, is greater than a CWST value for a surface of a layer of a filter material among the plurality of filter materials that is located closest to the other spout of the container, such surface being on the side with the other spout.

11. A blood processing filter according to claim 1, wherein the filter materials comprise nonwoven fabric.

12. A blood processing filter according to claim 9, wherein the polymer has a nonionic hydrophilic group and a basic nitrogen-containing functional group, and the amount of basic nitrogen atoms in the polymer coating layer is from 0.2 to 8.0 mass %.

13. A blood processing filter according to claim 9, wherein the polymer has a functional group comprising a zwitterion.

14. A blood processing filter according to claim 13, wherein the functional group comprising a zwitterion is a functional group derived from at least one type of compound selected from the group consisting of carbobetaine, sulfobetaine, and phosphobetaine.

15. A blood processing filter according to claim 13, wherein the polymer comprises a monomer unit (1) having a nonionic group, a monomer unit (m) having a basic nitrogen-containing functional group, and a monomer unit (n) including a zwitterion.

16. A method for manufacturing a blood processing filter according to claim 1, the method comprising: preparing a filter base material; and coating both the surface A and surface B of the base material with a hydrophilic polymer using a gravure coating method.

* * * * *